(12) United States Patent
Payton et al.

(10) Patent No.: US 9,445,739 B1
(45) Date of Patent: Sep. 20, 2016

(54) SYSTEMS, METHODS, AND APPARATUS FOR NEURO-ROBOTIC GOAL SELECTION

(75) Inventors: David W. Payton, Calabasas, CA (US); Michael J. Daily, Thousand Oaks, CA (US)

(73) Assignee: HRL Laboratories, LLC, Malibu, CA (US)

( * ) Notice: Subject to any disclaimer, the term of this patent is extended or adjusted under 35 U.S.C. 154(b) by 1625 days.

(21) Appl. No.: 12/699,649

(22) Filed: Feb. 3, 2010

(51) Int. Cl.
*A61B 5/04* (2006.01)
*A61B 5/0476* (2006.01)

(52) U.S. Cl.
CPC .................................. *A61B 5/0476* (2013.01)

(58) Field of Classification Search
USPC ........ 700/245; 600/300, 595, 544, 411, 407, 600/410; 434/236; 128/731, 732; 607/54, 607/45
See application file for complete search history.

(56) References Cited

U.S. PATENT DOCUMENTS

| | | | |
|---|---|---|---|
| 5,363,858 A * | 11/1994 | Farwell | 600/544 |
| 5,467,777 A * | 11/1995 | Farwell | 600/544 |
| 7,209,788 B2 | 4/2007 | Nicolelis et al. | |
| 7,260,430 B2 * | 8/2007 | Wu et al. | 600/545 |
| 7,392,079 B2 | 6/2008 | Donoghue et al. | |
| 8,069,125 B2 * | 11/2011 | Jung et al. | 706/11 |
| 2002/0058867 A1 * | 5/2002 | Breiter et al. | 600/407 |
| 2002/0103429 A1 * | 8/2002 | deCharms | 600/410 |
| 2004/0073414 A1 | 4/2004 | Bienenstock et al. | |
| 2004/0267320 A1 | 12/2004 | Taylor et al. | |
| 2005/0273890 A1 | 12/2005 | Flaherty et al. | |
| 2009/0156907 A1 * | 6/2009 | Jung et al. | 600/300 |

OTHER PUBLICATIONS

Bayliss et al., "Changing the P300 Brain Computer Interface," CyberPsychology & Behavior, vol. 7, No. 6, 2004, pp. 694-704.
Jessica D. Bayliss, "Use of the Evoked Potential P3 Component for Control in a Virtual Apartment," IEEE Transactions on Neural Systems and Rehabilitation Engineering, vol. 11, No. 2, Jun. 2003, pp. 113-116.
Berka et al., "Real-Time Analysis of EEG Indexes of Alertness, Cognition, and Memory Acquired With a Wireless EEG Headset," International Journal of Human-Computer Interaction, vol. 17, No. 2, 2004, pp. 151-170.
Berka et al., "EEG Indices Distinguish Spatial and Verbal Working Memory Processing: Implications for Real-Time Monitoring in a Closed-Loop Tactical Tomahawk Weapons Simulation," First International Conference on Augmented Cognition, Jul. 2005, 10 pages.
Berka et al., "EEG quantification of alertness: Methods for early identification of individuals most susceptible to sleep deprivation," Proceedings of the SPIE Defense and Security Symposium, Biomonitoring for Physiological and Cognitive Performance during Military Operations, vol. 5797, 2005, pp. 78-89 (12 pages).

(Continued)

*Primary Examiner* — Ronnie Mancho
(74) *Attorney, Agent, or Firm* — Hanley, Flight & Zimmerman, LLC

(57) ABSTRACT

Systems, methods, and apparatus for neuro-robotic goal selection are disclosed. An example method to control a robot is described, including presenting a target object to a user, the target object corresponding to a goal to be effectuated by a robot, emphasizing a portion of the target object, identifying a first brain signal corresponding to a first mental response of the user to the emphasized portion, determining whether the first mental response corresponds to a selection of the emphasized portion by the user, and effectuating the robot with respect to the goal based on the emphasized portion.

20 Claims, 9 Drawing Sheets

(56) References Cited

OTHER PUBLICATIONS

Berka et al., "Implementation of a Closed-Loop Real-Time EEG-Based Drowsiness Detection System: Effects of Feedback Alarms on Performance in a Driving Simulator," Proceedings of the International Conference on Human Computer Interaction, Jul. 2005, 10 pages.
Cheng et al., "Design and Implementation of a Brain-Computer Interface With High Transfer Rates," IEEE Transactions on Biomedical Engineering, vol. 49, No. 10, Oct. 2002, pp. 1181-1186.
Cichocki et al., "Noninvasive BCIs: Multiway Signal-Processing Array Decompositions," IEEE Computer Society, Oct. 2008, pp. 34-42.
Donchin et al., "The Mental Prothesis: Assessing the Speed of a P300-Based Brain-Computer Interface," IEEE Transactions on Rehabilitation Engineering, vol. 8, No. 2, Jun. 2000, pp. 174-179.
Gerson et al., "Cortically-coupled Computer Vision for Rapid Image Search," IEEE Transactions on Neural Systems and Rehabilitation Engineering, vol. 14, No. 2, Jun. 2006, pp. 174-179.
Lalor et al., "Steady-State VEP-Based Brain-Computer Interface Control in an Immersive 3D Gaming Environment," EURASIP Journal on Applied Signal Processing, 2005, pp. 3156-3164.
David G. Lowe, "Distinctive Image Features from Scale-Invariant Keypoints," International Journal of Computer Vision, Jan. 5, 2004, pp. 91-110.
Martinez et al., "Fully-Online, Multi-Command Brain Computer Interface with Visual Neurofeedback Using SSVEP Paradigm," Laboratory for Advanced Brain Signal Processing, RIKEN Brain Science Institute, 2007, 28 pages.
Schogl et al., "BioSig: A Free and Open Source Software Library for BCI Research," IEEE Computer Society, 2008, pp. 44-50.
Wolpaw et al., "Control of a two-dimensional movement signal by a noninvasive brain-computer interface in humans," PNAS, vol. 101, No. 51, Dec. 21, 2004, pp. 17849-17854.
Jonathan R. Wolpaw, "Brain-computer interfaces as new brain output pathways," The Journal of Physiology, 579, 2007, pp. 613-618.
Bell et al., "Control of a humanoid robot by a noninvasive brain-computer interface in humans," Journal of Neural Engineering, 2008 pp. 214-220.

Jonathan Sherwood, "Give it a Thought—and Make it so," University of Rochester, Brain-Computer Interface and Virtual Reality, May 3, 2000, 2 pages.
Khosla et al., "Spatio-temporal EEG source localization using simulated annealing," IEEE Trans Biomed Eng, 44 (11):1075-1091. 2007 (17 pages).
Khosla et al., "An iterative Bayesian maximum entropy method for the EEG inverse problem," In: EA Hoffman (Ed), Physiology Function from Multidimensional Images. Proc SPIE Medical Imaging, 1997 pp. 147-158.
Khosla et al., "Three-dimensional EEG source imaging via maximum entropy method," In IEEE Nuclear Science Symposium and Medical Imaging Conference Record, 1995, vol. 3: pp. 1515-1519.
Kholsa et al., "Spatial mislocationsation of EEG electrodes—effects on accuracy of dipole estimation," Clin Neurophysiol, 1999, 110(2): pp. 261-271.
Kholsa et al. Bio-inspired visual attention and object recognition, Proc. SPIE 6560, 656003, (2007) 11 pages.
Kholsa et al. A bio-inspired system for spatio-temporal recognition instatic and video imagery Proc. SPIE 6560, 656002, (2007) 8 pages.
Srinivasa et al., "A Self-Organizaing Neural Model for Fault Tolerant Control of Redundant Robots," In Proceedings of the IEEE International Joint Conference on Neural Networks, pp. 483-488, 2007.
Srinivasa et al., "A Bio-Inspired Kinematic Controller for Obstacle Avoidance during reaching tasks with Redundant Robots," to apper in IEEE BioRob2008 confernce, Scottsdale AZ, 8 pages.
McFarland et al., "Electroencephalographic (EEG) Control of Three-Dimensional Movement," In Soc. for Neuroscience Abstract, 2008.
Parra et al., "Recipes for the linear analysis of EEG," NeuroImage 28, 2005, pp. 326-341.
Parra et al., "Adaptive Brain Computer-Interface 1. For Augmented Cognition and Action," http://liinc.bme.columbia.edu/~augcog/, retrieved online Jun. 16, 2010, 3 pages.
United States Patent and Trademark Office, "Office action", issued Apr. 26, 2012, in connection with U.S. Appl. No. 12/699,660, (22 pages).

\* cited by examiner

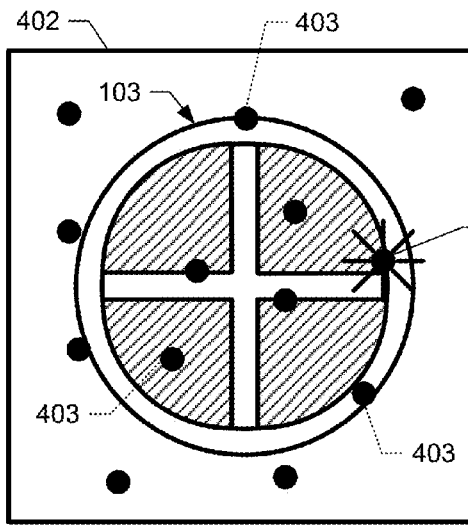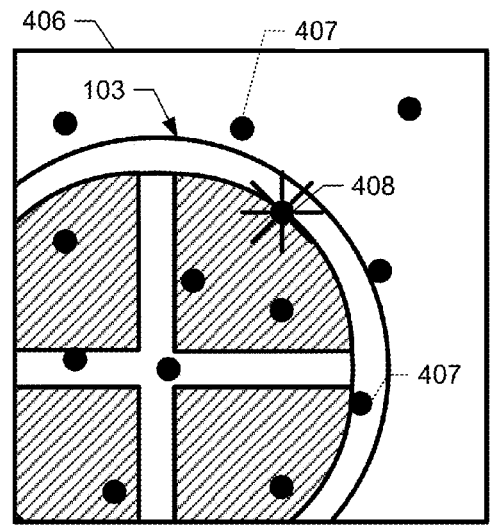
FIG. 4A  FIG. 4B
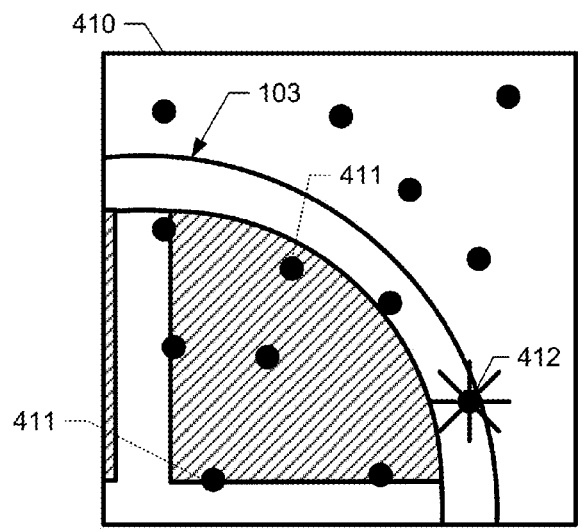
FIG. 4C

SYSTEMS, METHODS, AND APPARATUS FOR NEURO-ROBOTIC GOAL SELECTION

FIELD OF THE DISCLOSURE

This disclosure relates generally to brain-controlled human-machine interfaces and, more particularly, to systems, methods, and apparatus for neuro-robotic goal selection.

BACKGROUND

In the field of robotic control, current control methods are problem-specific. Thus, a particular task requires specialized robotic control methods, and there are no general solutions that may be applied to many different problem situations and robot configurations. Specialized control methods are often brittle and do not easily adapt to unforeseen circumstances.

Electroencephalograms (EEGs) are often used in brain-based interfaces to decode neural activity within the brain. EEGs are non-invasive and produce rapid responses to stimuli. EEG brain-based control techniques can be divided into two classes: endogenous and exogenous. For endogenous techniques, a subject employs imagination to evoke a particular brain wave pattern, which is measured by the EEG. However, endogenous methods require a long training period for the user to learn to produce distinguishable mental responses.

Exogenous techniques use external stimuli to evoke a desired EEG response. The exogenous techniques require far less user training than endogenous techniques. One particular neural response, the P300 signal, is reliably and robustly detected by the EEG. The P300 signal is a manifestation of a mental response to unpredictable stimuli in an oddball paradigm, such as an expected event occurring at an unexpected time.

BRIEF SUMMARY

Systems, methods, and apparatus for neuro-robotic goal selection are described herein. Some example methods to control a robot include presenting a target object to a user, the target object corresponding to a goal to be effected by a robot, emphasizing a portion of the target object, identifying a first brain signal corresponding to a first mental response of the user to the emphasized portion, determining whether the first mental response corresponds to a selection of the emphasized portion by the user, and controlling the robot based on determining that the first mental response corresponds to a selection of the emphasized portion.

In some example articles of manufacture, machine readable instructions are included thereon which, when executed, cause a machine to present a target object to a user, the target object corresponding to a goal to be effected by a robot, emphasize a portion of the target object, identify a first brain signal corresponding to a first mental response of the user to the emphasized portion, determine whether the first mental response corresponds to a selection of the emphasized portion by the user, and control the robot based on determining that the first mental response corresponds to a selection of the emphasized portion.

Some example methods further include presenting a plurality of physical configurations capable of reaching the goal to the user, emphasizing one of the plurality of physical configurations of the target object, identifying a second brain signal corresponding to a second mental response of the user to an emphasized physical configuration, determining whether the second mental response corresponds to a selection of the emphasized physical configuration by the user, and generating a constraint on the robot corresponding to the emphasized physical configuration in response to determining the emphasized physical configuration. In some example methods, presenting the target object to the user includes generating an image of the target object, selecting a plurality of features of the target object, and displaying the target object and the features to the user. In some examples, emphasizing the features of the target object includes selecting one of the plurality of features and flashing or flickering the selected feature over the image.

In some example methods, identifying the first brain signal includes monitoring an electroencephalogram (EEG) for at least one of a P300 brain signal or a steady-state visual evoked potential. In some examples, controlling the robot is in response to receiving the P300 response to the emphasized portion. Some example methods further include presenting a second view of the target object to the user, wherein the second view is based on the emphasized portion, emphasizing a second portion of the second view, identifying a second brain signal corresponding to a second mental response of the user to the emphasized second portion, and determining whether the second mental response corresponds to a selection of the emphasized second portion by the user, wherein controlling the robot is based on the emphasized second portion. In some examples, presenting the target object to the user includes displaying a plurality of markers at different locations, the markers comprising different frequencies. In some examples, identifying the first mental response of the user comprises monitoring an EEG for the first mental response corresponding to one of the plurality of markers. In some example methods, controlling the robot comprises controlling the robot to move toward the portion of the target object corresponding to the marker, where the marker corresponds to the first mental response.

Some example robot control apparatus are also described, which include a goal/constraint selector, a user response interface, and a robot interface. The example goal/constraint selectors generate a first image of a target object, to identify a plurality of features based on the first image, to emphasize one of the plurality of features to a user, to modify the first image based on a feature selected by the user, to present a plurality of physical configurations to the user, and to emphasize one of the plurality of physical configurations to the user. Some example user response interfaces are coupled to the goal/constraint selector, and identify a user brain signal in response to an emphasized feature or physical configuration. Some example robot interfaces are coupled to the user response interface to generate control information to control a robot based on at least one of the emphasized feature or the emphasized physical configuration corresponding to an identified brain signal.

In some examples, the user response interface identifies a user brain signal corresponding to a negative selection of the emphasized physical configuration. Some example robot control apparatus further include a user display to display the plurality of robot configurations to the user, where the user response interface measures the user response to one of the robot configurations when the robot configuration is emphasized to determine an undesirable robot configuration. In some examples, the goal/constraint selector includes an image generator to generate a current reference image based on the target object and one or more parameters, a feature generator coupled to the image generator to generate features of the target object based on the current reference image, a feature/image presenter coupled to the image and feature generators to provide the reference image and the features to a user display, and a parameter generator coupled to the feature generator and the user response interface to generate the one or more parameters of the reference image based on the target object.

In some example robot control apparatus, a feature includes at least one of a portion of the target object or a marker. In some examples, the user response interface comprises an electroencephalogram (EEG). In some example apparatus, the brain signal includes one of a P300 signal or a steady-state visual evoked potential. In some examples, the goal/constraint selector modifies the first image by generating a second image based on the feature selected by the user and identifies a second plurality of features based on the second image, and the user response interface identifies a second user brain signal in response to a second emphasized feature. In some examples, the second image is a zoomed in version of the first image.

Some described example systems to control a robot include a robot, an object modeler, a goal/constraint selector, an electroencephalogram (EEG) system, a classifier, and a robot controller. In some examples, the robot effects an end goal, and the object modeler generates a three-dimensional object model of the target object. Some example goal/constraint selectors are coupled to the object modeler, and receive the object model, generate an image of the target object, analyze the target object to generate a plurality of features or configurations, display the image and the features or configurations to a user, emphasize one of the features or configurations at a time, and determine an end goal on the target object to be effected by the robot and one or more undesirable physical configurations of the robot. Some example EEG systems monitor the user for a mental response. In some examples, the classifier identifies a user selection of a feature or a user selection of an undesirable configuration based on the mental response. In some examples, the robot controller is coupled to the goal/constraint selector and controls the robot to move toward the target object in response to identifying the end goal and an undesirable robot configuration.

BRIEF DESCRIPTION OF THE DRAWINGS

FIGS. 4A-4C illustrate example images wherein the feature generator of FIG. 2 determines features randomly and generates the features to correspond to portions of the image.

DETAILED DESCRIPTION

Figure 1:
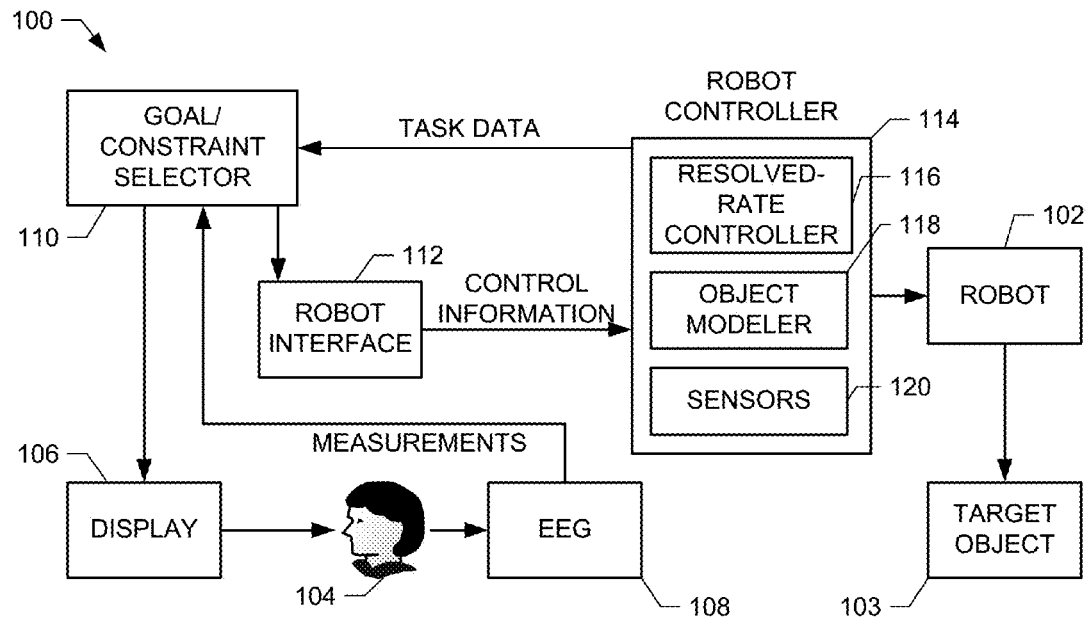
FIG. 1 is a block diagram of an example robot control system.

Certain examples are shown in the above-identified figures and described in detail below. In describing these examples, like or identical reference numbers may be used to identify common or similar elements. The figures are not necessarily to scale and certain features and certain views of the figures may be shown exaggerated in scale or in schematic for clarity and/or conciseness. Although the following discloses example systems, methods, and apparatus, it should be noted that such systems, methods, and apparatus are merely illustrative and should not be considered as limiting. The example circuits described herein may be implemented using discrete components, integrated circuits (ICs), hardware that is programmed with instructions, or any combination thereof. Accordingly, while the following describes example systems, methods, and apparatus, persons of ordinary skill in the art will readily appreciate that the examples are not the only way to implement such systems, methods, and apparatus.

The example systems, methods, and apparatus described herein provide a robust, brain-in-the-loop solution to control robot activities. The example systems, methods, and apparatus incorporate human judgment into a control activity to utilize human experience and problem-solving, which allows a more flexible, yet robust, control solution. In contrast to previous robot control systems that allow selection between multiple objects, the example systems, methods, and apparatus described below allow selection of both positive goals and negative goals, or constraints, by the user in addition to allowing selection of a precise goal on a target object. The example systems, methods, and apparatus further allow selection of the goals and constraints without the use of physical controls (e.g., a joystick). Therefore, the example systems, methods, and apparatus may be adapted to many different tasks and many different variations of the tasks. Example applications may include, but are not limited to, space operations, manufacturing, hazardous waste processing and removal, improvised explosive device (IED) disassembly, and prosthetics. Additionally, while the following description includes an example related to robotic arm control, the control techniques and systems described herein are not necessarily limited to such an example implementation.

In some described example apparatus, a user selects one or more features to control a robot. A modeler generates a model of the target object or the end goal. Based on the model, an image generator generates an image of the model for display to a user.

A feature generator determines several features based on the current image of the model and a feature and image presenter presents the image of the object and an overlay image of the features to a user, who is monitored via an electroencephalogram (EEG) system. The user identifies a goal on the image, and mentally selects a feature corresponding to the goal. While the user concentrates on the feature, the feature and image presenter emphasizes the candidate features in a random sequence. When the feature on which the user is concentrating is emphasized, the EEG system measures brain signals from the user and a classifier identifies the brain signals as a mental response (e.g., a P300 signal).

Based on the mental response, a parameter generator identifies parameters associated with the selected feature and constructs parameters for a new image. The image generator zooms and/or pans the previous image based on the parameters to generate the new image and the feature generator reanalyzes the new image to determine new features consistent with the new image. The zoom, pan, and reanalyze process repeats while the user continues to select features. Each time the process repeats, the robot physically moves with respect to the end goal or the image of the object is zoomed (e.g., closer) to allow more precise selection, or the robot may wait to move until the goal is selected with sufficient precision. When the robot is a sufficient distance with respect to the target object and/or the goal is selected with sufficient precision, the example system effects an end goal on the target object.

In addition to generating features representing an end goal, the example feature generator can generate one or more robot configurations to reach the end goal. The feature and image presenter presents an image of the target object and the robot configurations to the user. The user then selects an undesirable configuration, such as a configuration that carries a high risk of collision with an obstacle disposed between the robot and the goal. While the user concentrates on the undesired configuration, the feature and image presenter emphasizes the candidate configurations in a random order. When the undesired configuration on which the user is concentrating is emphasized, the classifier identifies a mental response (e.g., a P300 signal) from user brain waves measured by the EEG system. The parameter generator then sets a constraint on the robot configurations to avoid the undesired configuration identified by the mental response. In some examples, the user may positively select a desired configuration instead of selecting an undesired configuration. When the end goal and configuration constraints are established, the robot may approach the target object and/or effect the end goal according to the constraints.

FIG. 1 is a block diagram of an example robot control system 100. The robot control system 100 controls a robot 102 to reach a target object 103. When relatively far from the target object 103, the robot 102 may use broad and imprecise movements. A user 104 interacts with the robot control system 100 by viewing the target object 103 via a display 106 and selecting goals and constraints via an EEG system 108. The display 106 presents an image of the target object 103 and several features to the user 104. Alternatively, the user 104 may view the actual target object 103 through goggles or directly, and the display 106 presents a heads up display (HUD) to overlay the features onto the target object 103. The user 104 uses his or her experience and knowledge to identify one of the features as a goal. As explained in detail below, while the user 104 identifies and concentrates on a feature, the EEG system 108 measures the user's 104 brain waves which may be used to identify particular mental responses that correspond to a selection of an emphasized feature by the user 104. Thus, when the feature concentrated upon by the user 104 is emphasized by the system 100, the system 100 detects the user's 104 brain signals (e.g., a P300 signal) indicating that the emphasized feature matches the feature on which the user 104 is concentrating.

A goal/constraint selector 110 determines the goals and constraints selected by the user 104. As described below, the goal/constraint selector 110 receives an operating mode, and either an object model or one or more images of the target object 103. Based on the operating mode, the goal/constraint selector 110 presents an image of the target object 103 to the user 104 along with several potential goals and/or constraints (i.e., features). The goal/constraint selector 110 then emphasizes the potential goals or constraints until a mental response (e.g., a P300 response) is identified from EEG measurements from the EEG system 108 to identify one of the potential goals or constraints on which the user 104 was concentrating. Based on the goal or constraint selected by the user 104, the goal/constraint selector 110 provides additional goals or constraints to the user 104, and/or sends commands to a robot interface 112. In some examples, the goal/constraint selector 110 generates new goals or constraints for presentation to the user 104.

The goal/constraint selector 110 determines an approximate goal selected or identified by the user 104, which will position the robot 102 close to the target object 103. The goal/constraint selector 110 also provides for the consideration of one or more constraints, which will prevent any physical configurations or movements of the robot 102 from causing a collision. After the goal/constraint selector 110 establishes at least one approximate or precise goal and any desired physical configuration constraints, the goal/constraint selector 110 may provide commands and parameters to control the robot 102 to partially effect the end goal (e.g., to move the robot 102 partially toward the target object 103). Alternatively, the goal/constraint selector 110 may issue a batch command when the user 104 has identified a more specific goal via multiple goal selections.

When the goal/constraint selector 110 has established a precise goal, the goal/constraint selector 110 may provide commands and parameters to control the robot 102 to fully effect the goal. The commands and/or parameters from the goal/constraint selector 110 are translated by the robot interface 112. The translated commands and/or parameters may differ widely between different robot applications. The goal/constraint selector 110 is described in more detail in FIG. 2 below.

To interface the robot control system 100 to a given type of robot 102, the robot interface 112 translates the commands and parameters generated by the goal/constraint selector 110 to robot control information. For example, a grappling robot arm may include a different command structure than, for example, a welding robot arm or a humanoid robot. Thus, the robot interface 112 translates parameters and commands from the goal/constraint selector 110 to parameters and commands suitable for the particular type of robot 102.

A robot controller 114 receives control information from the robot interface 112 and controls the robot 102 with respect to an end goal or task defined by the control information. In the example of FIG. 1, the robot controller 114 includes a resolved-rate controller 116 and an object modeler 118. As explained below, based on the data determined by the resolved-rate controller 116, and/or the object modeler 118, the robot controller 114 provides task data, such as model data generated by the object modeler 118 and/or the distance from the robot 102 to the target object 103, to the goal/constraint selector 110. The robot controller 114 may determine the distance from the robot 102 to the target object 103 using any desired method.

The resolved-rate controller 116 controls the robot 102 via calculated robot joint velocities. In other words, the resolved-rate controller 116 receives a goal position for the robot 102, determines a physical configuration for the robot 102 to achieve the goal, and controls the robot 102 to achieve the physical configuration. The resolved-rate controller 116 may also consider limitations on physical joint configurations when determining physical configurations.

The object modeler 118 identifies and generates a model of the target object 103. For example, the object modeler 118 may visually scan the exterior of the target object 103 to determine three-dimensional point cloud data. The object modeler 118 may scan using, for example, a laser scanner to determine the contours of the target object 103. While the object modeler 118 is shown as included in the robot controller 114, the object modeler 118 may be a separate system or component to generate a model of the target object 103 and provide the model to the goal/constraint selector 110.

The example robot controller 114 further includes one or more sensors 120 to provide information about the robot 102 to the goal/constraint selector 110, the resolved-rate controller 116, and/or the object modeler 118. In some examples, the sensors 120 measure and/or identify the position(s) of the robot 102, the velocity of the robot 102, the angular positions of the robot 102 with respect to a reference, and/or any other information about the robot 102 that may be useful for controlling the robot 102 to effect the end goal (e.g., move toward the target object 103). In some examples, one or more of the sensors 120 are included on the robot 102.

In some examples, the sensors 120 provide positional (and other) information for the robot 102 with respect to the target object 103 to the resolved-rate controller 116 and the goal/constraint selector 110. The object modeler 118 may then be removed, and the goal/constraint selector 110 determines the goal and one or more configuration constraints using the information from the sensors 120 instead of a model of the target object 103. In some other examples, the object modeler 118 and the information provided by the sensors 120 is redundant to prevent collisions between the robot 102 and the target object 103.

The goal/constraint selector 110 determines goals and constraints for use in effecting the end goal via the robot 102. For example, the goal/constraint selector 110 presents features to the user 104, detects selection of one of the features by the user 104, and generates parameters used by the robot controller 114.

In an example of operation, the robot 102 is a relatively far distance (e.g., >15 centimeters (cm)) from the target object 103. The object modeler 118 performs an analysis of the target object 103 to determine the contours of the target object 103. The robot controller 114 sends the task data, including the distance from the robot 102 to the target object 103 and the object model, to the goal/constraint selector 110.

The goal/constraint selector 110 generates an image and several features of the target object 103. The image and features are displayed via the display 106 to the user 104, who determines a goal and/or a configuration constraint on the robot 102. While the user 104 determines the goal and/or configuration, the goal/constraint selector 110 emphasizes the features. The EEG system 108 measures brain signals of the user 104 as the features are emphasized. The measurements are provided to the goal/constraint selector 110, which identifies a particular mental response from the measurements corresponding to a user selection of an emphasized goal or constraint. The goal/constraint selector 110 then generates a goal or constraint based on the particular feature the user 104 concentrates on. The goal/constraint selector 110 may iteratively interact with the user 104 to determine the goal and any configuration constraints, and then transmits parameters and/or commands to the robot interface 112.

The robot interface 112 translates the parameters and/or commands into control information usable by the robot controller 114. Based on the control information, the robot controller 114 (e.g., via the resolved-rate controller 116) controls the robot 102. The robot control device 100 may repeat operation to move the robot 102 with respect to the target object 103, if necessary.

When the goal/constraint selector 110 has determined a precise goal location and/or configuration constraints, the goal/constraint selector 110 sends the parameters and/or commands to the robot interface 112. The robot interface 112 translates the parameters and/or commands and provides the translated parameters and/or commands to the robot controller 114. As a result, the robot 102 moves toward the target object 103 at a position and according to configuration constraints defined by the user 104 in a controlled manner.

Figure 2:
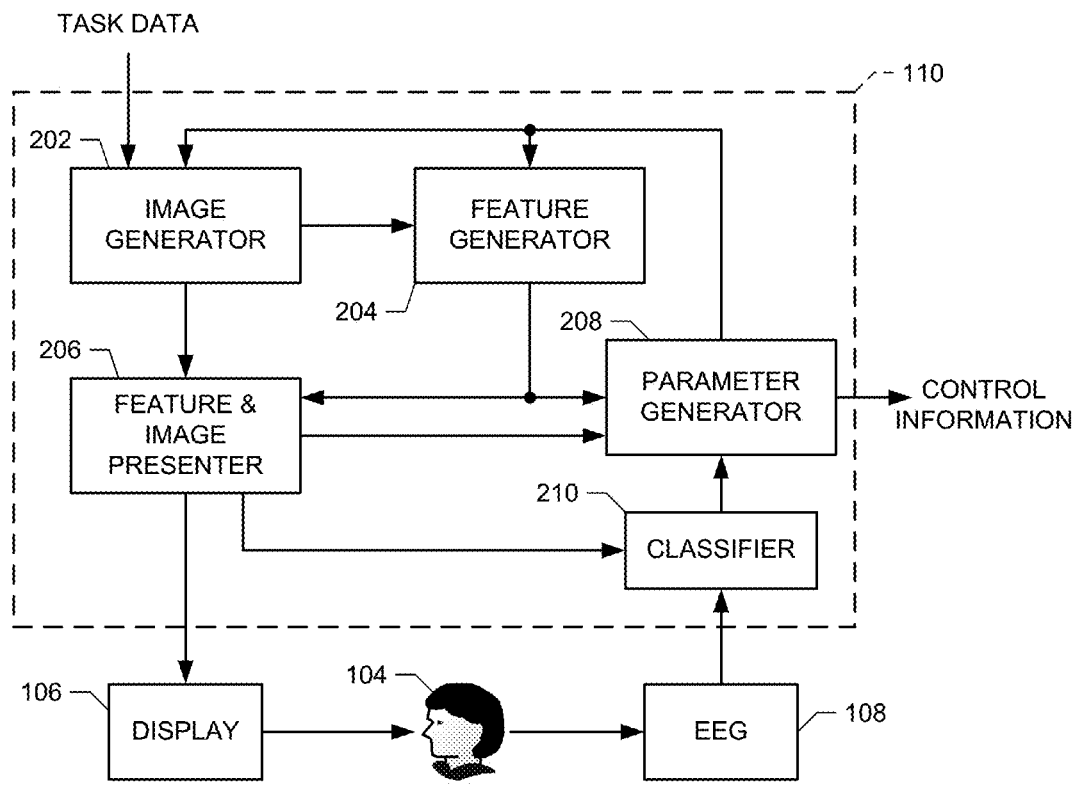
FIG. 2 is a more detailed block diagram of the goal/constraint selector illustrated in FIG. 1.

FIG. 2 is a more detailed block diagram of the goal/constraint selector 110 illustrated in FIG. 1. Generally, the goal/constraint selector 110 receives mode selection data and/or an object model of the target object 103, and provides an image of the target object 103 to a user 104 via the display 106, emphasizes features of the target object 103, and generates parameters to control the robot 102 based on the user's 104 selection. To this end, in one example implementation, the goal/constraint selector 110 includes an image generator 202, a feature generator 204, a feature and image presenter 206, a parameter generator 208, and a classifier 210. An EEG system 108 measures the mental response of the user 104 to an emphasized feature, and the goal/constraint selector 110 determines a goal or a constraint based on user selection (via mental response) of an emphasized feature.

The image generator 202 receives the object model and mode selection information from the goal/constraint selector 110 of FIG. 1. Based on the object model, the image generator 202 generates an image of the target object 103. The image serves as a reference image to the user 104. If the model of the target object 103 is a three-dimensional model, the image generator 202 generates one view of the target object 103. Additionally, if any goals or constraints have been selected by the user 104, the image generator 202 adjusts the image or viewpoint. In some examples, the user 104 may choose to alter the view of the target object 103 if the view generated by the image generator 202 is not adequate.

The feature generator 204 receives the object model, the mode select, and/or the image data from the image generator 202. Based on the object model and/or the image data, the feature generator 204 determines one or more features of the target object 103. A feature may refer to, for example, a particular portion of the image generated by the image generator 202, a particular portion of the target object 103 as determined from the object model, or, more generally, any individually-identifiable portion of an image or object. The features are overlaid on the image of the target object 103 for presentation to the user 104. Features may be determined analytically or randomly. For example, the feature generator 204 may determine that particular features of the image and/or model are particularly conducive to the current robotic task. To this end, the feature generator 204 may perform feature extraction, image segmentation, and/or volume segmentation on the target object 103 model. Alternatively, the feature generator 204 may randomly select a number of points on the image as features.

The image and feature presenter 206 determines how the features are emphasized to the user 104 on the display 106. In some examples, the image and feature presenter 206 presents the target object 103 image or viewpoint in the background, and highlights one of the features to the user at a time. In other examples, the image and feature presenter 206 presents the target object 103 image or viewpoint in the background, and overlays markers at locations on the image corresponding to the features. The markers may be flashed one at a time, multiple markers may be flashed simultaneously, and/or the markers may all flash at different frequencies (from 5 Hz to 45 Hz). In some examples, the image and feature presenter 206 is implemented using rapid serial visual presentation (RSVP), which is available in the E-Prime® software package, a commercial stimulus presentation package sold by Psychology Software Tools, Inc.

While the image is displayed on the display 106, the user 104 focuses on a feature that is closest to the desired end goal. As the image and feature presenter 206 emphasizes one of the features at a time on the display 106, the user 104 expects to see the feature as the EEG system 108 monitors the user's 104 brain waves and provides the brain wave measurements to the classifier 210. If the image and feature presenter 206 emphasizes a feature not desired by the user 104, the classifier 210 does not detect or identify a response by the user 104 from the EEG system 108. However, if the image and feature presenter 206 emphasizes the feature desired by the user 104, the user's brain emits an electrical signal referred to as the P300 signal indicating recognition of the emphasized feature. The P300 signal response from the user 104 has approximately a 300 millisecond (ms) delay from the time the display 106 shows the emphasized feature. In this manner, the P300 signal acts as a "that's it!" signal indicating a match between the desire of the user 104 and the emphasis of the same.

While the image and feature presenter 206 emphasizes features on the display 106 for the user 104, the image and feature presenter 206 also provides the emphasized feature information to the parameter generator 208. Thus, when the classifier 210 detects the P300 signal from the EEG system 108 measurement and identifies the P300 signal as corresponding to a selection of an emphasized feature, the parameter generator 208 generates a goal parameter corresponding to the emphasized feature selected by the user 104. During goal selection, the parameter generator 208 sends the new parameter to the image generator 202 and the feature generator 204. Based on the parameter, the image generator 202 generates a new image for display to the user 104. For example, the image generator 202 may generate a closer view that is centered on the portion of the previous image corresponding to the selected feature (i.e., zoom and pan the image). The goal/constraint selector 110 iterates to generate an image, generate features of the image, display and emphasize the features to the user 104, detect a response to the emphasized feature, and generate a parameter based on the feature, until an uncertainty associated with the location of an end goal on the target object 103 is within suitable bounds.

The classifier 210 detects a user response by correlating the brain wave measurements from the EEG system 108 with an external stimulus such as the emphasis of a feature to the user 104. In examples using a P300 response, there is approximately a 300 ms delay between display or highlighting of a given trackable feature and the corresponding mental response. In some examples, multiple trackable features are displayed and/or highlighted within 300 ms and, thus, a mental response does not necessarily immediately follow emphasis of the user-desired trackable feature. Thus, the classifier 210 may evaluate the user's 104 mental response after highlighting all of the trackable features to determine which of the trackable features is most likely to have been selected by the user 104, and/or the classifier 210 may evaluate the user's mental response in real-time, taking into account the delay between highlighting of a given trackable feature and a corresponding mental response. When an appropriate mental response is detected, the classifier 210 provides an indication to the parameter generator 208 which of the emphasized features is the feature desired or selected by the user 104.

The goal/constraint selector 110 also generates negative goals, or constraints, selected by the user 104. Such negative goals may be used to disallow particular physical configurations and/or approach paths of the robot 102. Often, the number of acceptable physical configurations of the robot outnumbers the unacceptable configurations. When the user 104 is presented with several acceptable options, the user 104 may have difficulty invoking the proper mental response from which to identify the P300 signal. In contrast, when there are few unacceptable options and many acceptable options, the user 104 has little difficulty identifying and concentrating on one of the unacceptable options. The classifier 210 more easily identifies the user's 104 mental response to unacceptable configurations.

A more detailed description of the robot control system 100 and the goal/constraint selector 110 of FIGS. 1 and 2 is provided below. When beginning operation, the robot 102 is located relatively far away from the target object 103. The robot control system 100 allows broad and relatively imprecise movements of the robot 102 due to the low risk of collision with the target object 103. An example of brain-in-the-loop (i.e., neuro-robotic) control to effect a goal with the robot 102 is described below.

Figure 3A:
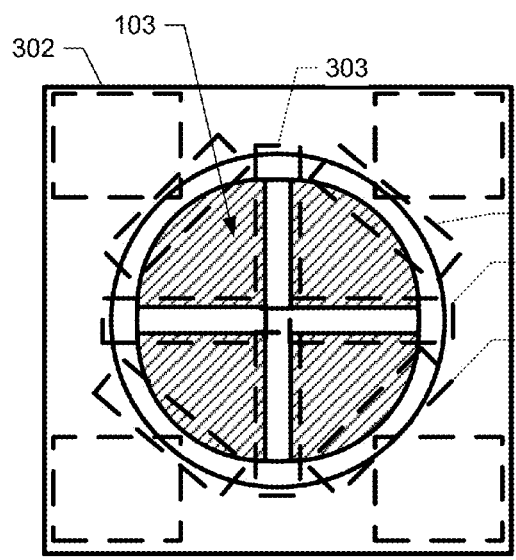
FIGS. 3A-3C illustrate example images wherein the feature generator of FIG. 2 determines features analytically and generates the features to correspond to sections of the target object.
Figure 3B:
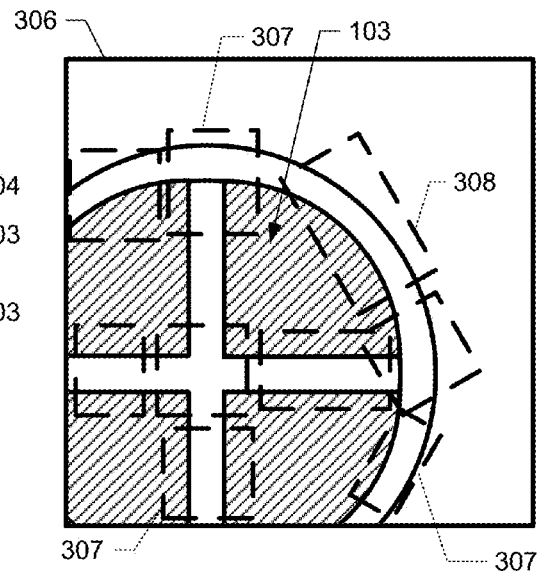
Figure 3C:
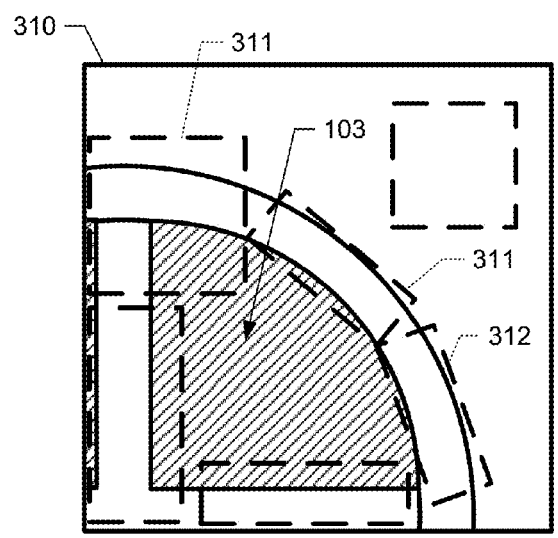

FIGS. 3A-3C and FIGS. 4A-4C are diagrams illustrating example images and features to select a goal on a target object 103. FIGS. 3A-3C illustrate example images 302, 306, 310 wherein the feature generator 204 determines features analytically and generates the features 303, 304, 307, 308, 311, 312 to correspond to sections of the target object 103. In an example of operation, the goal/constraint selector 110 is configured to generate features by analyzing an object model as shown in FIGS. 3A-3C. An example of goal selection will be described below, using the robot control system 100, the goal/constraint selector 110, and the example images and features illustrated in FIGS. 1, 2, 3A-3C, and 4A-4C.

The example object modeler 118 of FIG. 1 analyzes the example target object 103 and generates point cloud data. The point cloud data includes a large number of points that define the dimensions of the target object 103. The robot controller 114 determines task data including the current range from the robot 102 to the target object 103. The robot controller 114 then sends the task data, including object model data, to the goal/constraint selector 110.

Based on the object model, the image generator 202 generates a first image 302 of the target object 103. The image generator 202 provides the object model and the image 302 to the feature generator 204, which analyzes the object model and determines appropriate features. The image 302 and the features 304 are provided to the feature and image presenter 206. The feature and image presenter 206 provides the image 302 to the display 106 to show to a user 104.

The feature and image presenter 206 selects one or more features 303 and 304 and causes the display 106 to emphasize the features 303 and 304 to the user 104. For example, the feature 304 may blink or light up a portion of the image 302. As the features 303 and 304 are selected and emphasized to the user 104, the EEG system 108 measures the brain signals of the user 104. In the illustrated example, the classifier 210 identifies a mental response from the user 104 based on the measurements by the EEG system 108 when the feature and image presenter 206 emphasizes the feature designated 304.

As the feature and image presenter 206 selects a feature 304 for emphasis, the feature and image presenter 206 also updates the parameter generator 208 and the classifier 210 with the emphasized feature 304. The classifier 210 identifies a mental response by correlating the time at which the feature was emphasized with the brain wave measurements provided by the EEG system 108. After one or more features 303 and 304 are emphasized, the classifier 210 labels one of the emphasized features (e.g., the feature 304) as the selected feature if there is a corresponding mental response to the feature 304. If none of the emphasized features 303 and 304 is considered to be selected, the feature and image presenter 206 may emphasize the features 303 and 304 again or may consider the end goal to have been selected with sufficient precision for the robot 102 to effect the end goal (e.g., approach the target object 103). When the classifier 210 identifies the correct mental response as belonging to a selected feature, the parameter generator 208 generates a new parameter based on the location of the feature 304 and sends the parameter to the image generator 202 and the feature generator 204. For example, the parameter may include the location of the emphasized feature 304 and a size. If the feature generator 204 selects the features by analyzing the target object 103, the parameter may also identify the selected feature 304.

The image generator 202 then generates a new image 306, shown in FIG. 3B, of the target object 103 using the object model and the generated parameter. For example, the image generator 202 may zoom and pan the image 302 to a closer view of the selected feature 304. The closer view corresponds to a robot 102 position closer to the target object 103. Based on the new image 306, the feature generator 204 generates new features 307 and 308. For example, the feature generator 308 may analyze the previously selected feature and the corresponding portion of the object model to generate sub-features (e.g., the features 308) of the previously selected feature 304. The image 306 and the new features 307 and 308 are sent to the feature and image presenter 206, which presents the image 306 and the features 307 and 308 to the user 104. The user 104 selects an emphasized feature 308 (e.g., via the EEG system 108 and the classifier 210), and the parameter generator 208 generates a new parameter.

The image generator 202, the feature generator 204, the feature and image presenter 206, the parameter generator 208, the classifier 210, the display 106, and the EEG system 108 enable the user 104 to select another feature 312 from the next image 310. The image generator 202 generates the image 310 based on a parameter generated from the user selection of the feature 308. The example image generator 202, the example feature generator 204, the example feature and image presenter 206, the example parameter generator 208, the example display 106, the example EEG system 108, and the example user 104 may iterate the described process to more precisely determine an end goal on the target object 103. The example goal/constraint selector 110 then determines robot configuration constraints to limit the robot 102 from achieving any undesired positions as described below. When the end goal has been determine with sufficient precision and/or substantially low uncertainty and the configuration constraints have been selected, the example robot control system 100 effects the end goal (e.g., approaches the target object 103) via the selected goal location and constraints.

FIGS. 4A-4C illustrate example images 402, 406, 410 wherein the feature generator 204 determines features 403, 404, 407, 408, 411, 412 randomly and generates the features to correspond to portions of the image. In an example of operation, the goal/constraint selector 110 is configured to generate images and features by analyzing the object model as shown in FIGS. 4A-4C. The feature generator 204 receives an image 402 from the image generator 202 and randomly determines a plurality of features 404. The image 402 and the features 404 are provided to the feature and image presenter 206, which displays the image 402 and the features 404 via the display 106. In the example of FIG. 4A, the feature and image generator 206 displays the features 404 as markers overlaid on the image 402.

The feature and image presenter 206 emphasizes the example feature 404 by flashing or blinking the marker associated with the feature 404. The user 104 selects one of the features 404 in a similar manner as described above in FIGS. 3A-3C. The parameter generator 208 generates a selection parameter based on the selected feature 404. The image generator 202 and the feature generator 204 then generate a new image 406 and new features 408 based on the parameter. The example user 104 selects an emphasized feature 408 from the image 406, and the parameter generator 208 generates another selection parameter based on the selected feature 408. The new selection parameter is then used by the image generator 202 and the feature generator 204 to generate a third image 410 and another set of features 412.

The user 104 continues to select a feature from an image an uncertainty of the end goal location is within suitable bounds (e.g., the end goal is sufficiently precise). The example goal/constraint selector 110 then determines robot configuration constraints as described below. When the robot 102 is within a predetermined range of the target object 103 and the configuration constraints have been selected, the example robot control system 100 effects the end goal (e.g., approaches the target object 103) via the selected goal location and configuration constraints.

After the goal/constraint selector 110 determines a goal via user input, the goal/constraint selector 110 presents several potential configurations for the robot to achieve the goal. For example, the user 104 iteratively selects features on the target object 103 to choose a goal as the parameter generator 208 focuses on the target object 103. After selecting the end goal but prior to moving to robot 102 with respect to the goal, the goal/constraint selector 110 determines whether any potential configurations, such as approach vectors, are unacceptable.

Figure 5:
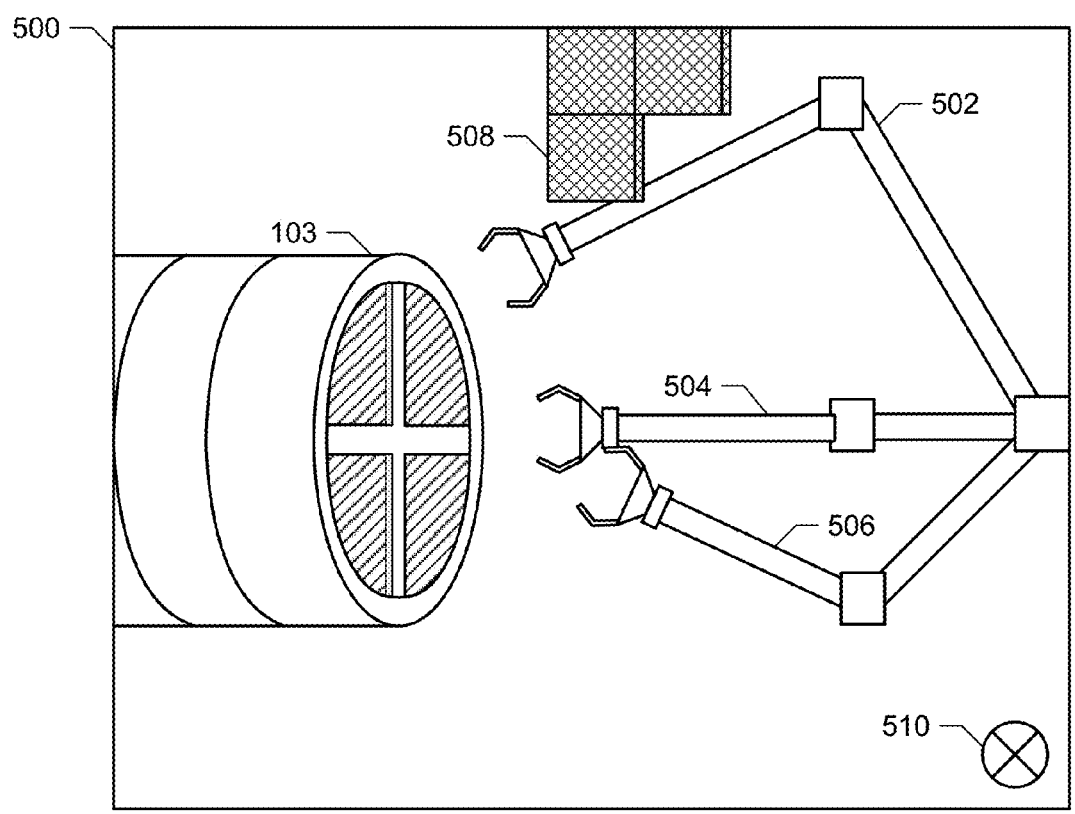
FIG. 5 is a diagram illustrating an example image and robot configurations.

FIG. 5 is a diagram illustrating an example image 500 and robot configurations 502, 504, 506. To determine whether any robot configurations are unacceptable, the image generator 202 generates a new image 500 of the target object 103. The image 500 may be generated from the same or a different perspective than the images 302, 306, and 310, based on whether the perspective of the images 302, 306, and 310 can accurately portray the potential robot configurations to the user 104.

The feature generator 204 then generates several configurations (i.e., features). During selection of robot configurations, the feature generator 204 determines potential robot configurations for display to the user 104. The image 500 and the robot configurations 502, 504, and 506 are sent to the feature and image presenter 206. The feature and image presenter 206 presents the image 500 and the robot configurations 502, 504, and 506 to the user 104 via the display 106. The feature and image presenter 206 emphasizes one of the configurations 502, 504, or 506 at a time. The feature generator 204 may also generate an accept feature 510 that the user 104 may select to indicate there are no remaining undesirable configurations.

The feature generator 204 may simulate multiple robot movements with respect to the end goal to determine the physical configurations. The simulation(s) may occur as the user 104 selects more precise end goals and configurations, and/or may occur after the user 104 has selected an end goal and positively or negatively selects different configurations for the robot to approach the end goal.

Figure 6:
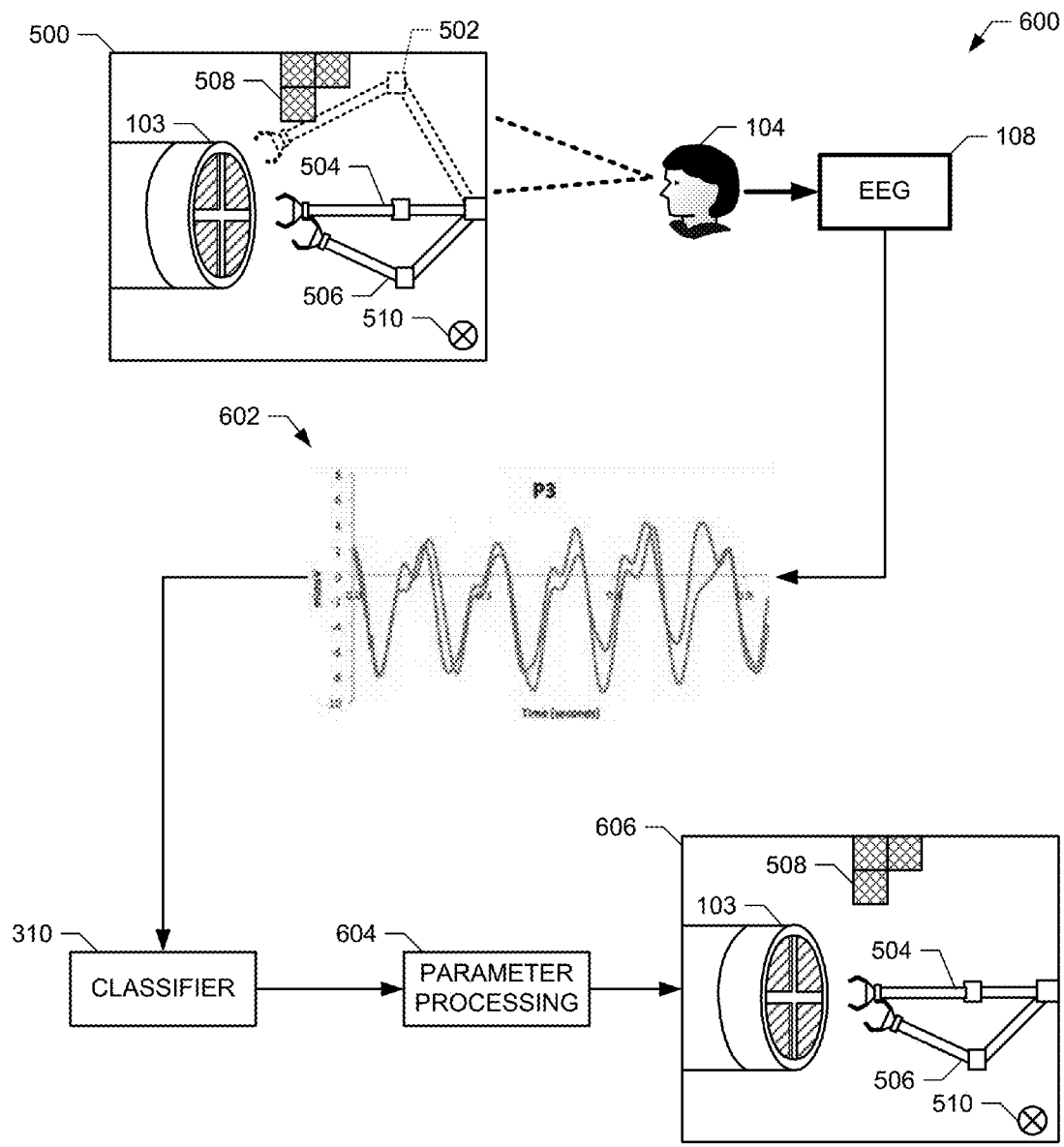
FIG. 6 illustrates an example data flow to identify an undesirable robot configuration from the example image of FIG. 5.

FIG. 6 illustrates an example data flow 600 to identify an undesirable robot configuration from the example image 500 of FIG. 5. In the example illustrated in FIG. 5, the robot configuration 502 is a high risk to strike an obstacle 508. However, the example configurations 504 and 506 offer little to no risk of collision. Therefore, the user 104 identifies the risk associated with the configuration 502 and concentrates on the configuration 502. When the feature and image presenter 206 emphasizes (e.g., flashes, blinks, flickers) the configuration 502, the EEG system 108 measures a brain signal 602 from the user 104 and provides the brain signal 602 to the classifier 210. The example classifier 210 identifies the emphasized configuration 502 as the configuration selected by the user 104. During the selection of constraints, the P300 operates as a "don't do that!" signal indicating a match between the user's 104 undesired configuration and the emphasized configuration. As a result, the parameter generator 208 eliminates the configuration 502 during parameter processing 604, and may also generate a parameter to prevent any configurations within a particular distance of the eliminated configuration 502.

The image generator 202 and the feature generator 204 may also generate a new image 606 and/or new features in response to the generated parameter. The user 104 may select either of the configurations 504 or 506 in addition to the configuration 502 if the configurations 504 or 506 have an unacceptable risk of collision or another adverse characteristic. If the user 104 is satisfied with the remaining configurations 504 and 506, the user 104 selects the accept feature 510.

The robot controller 114 of FIG. 1 may control the robot 102 with respect to the goal (e.g., move the robot 102 toward or away from the goal) after receiving one or more goals (e.g., an intermediate goal, an end goal). In some examples, the robot controller 114 does not move the robot 102 with respect to the goal until a sufficiently precise goal and any configuration constraints are selected by the user 104. Thus, the robot controller 114 performs a "batch" move, which uses the precise goal defined by the user as well as all constraints on movement. Alternatively, the robot controller 114 may move the robot 102 after each goal selection and configuration constraint selection by the user 104. Thus, the robot 102 moves incrementally with respect to the goal as the user 104 selects more precise goals. When the robot 102 moves sufficiently close to the target object 103 such that the end goal location is known to the robot controller 114 with a sufficiently low uncertainty, the example robot control system 100 effects the end goal (e.g., approaches the target object 103).

Figure 7:
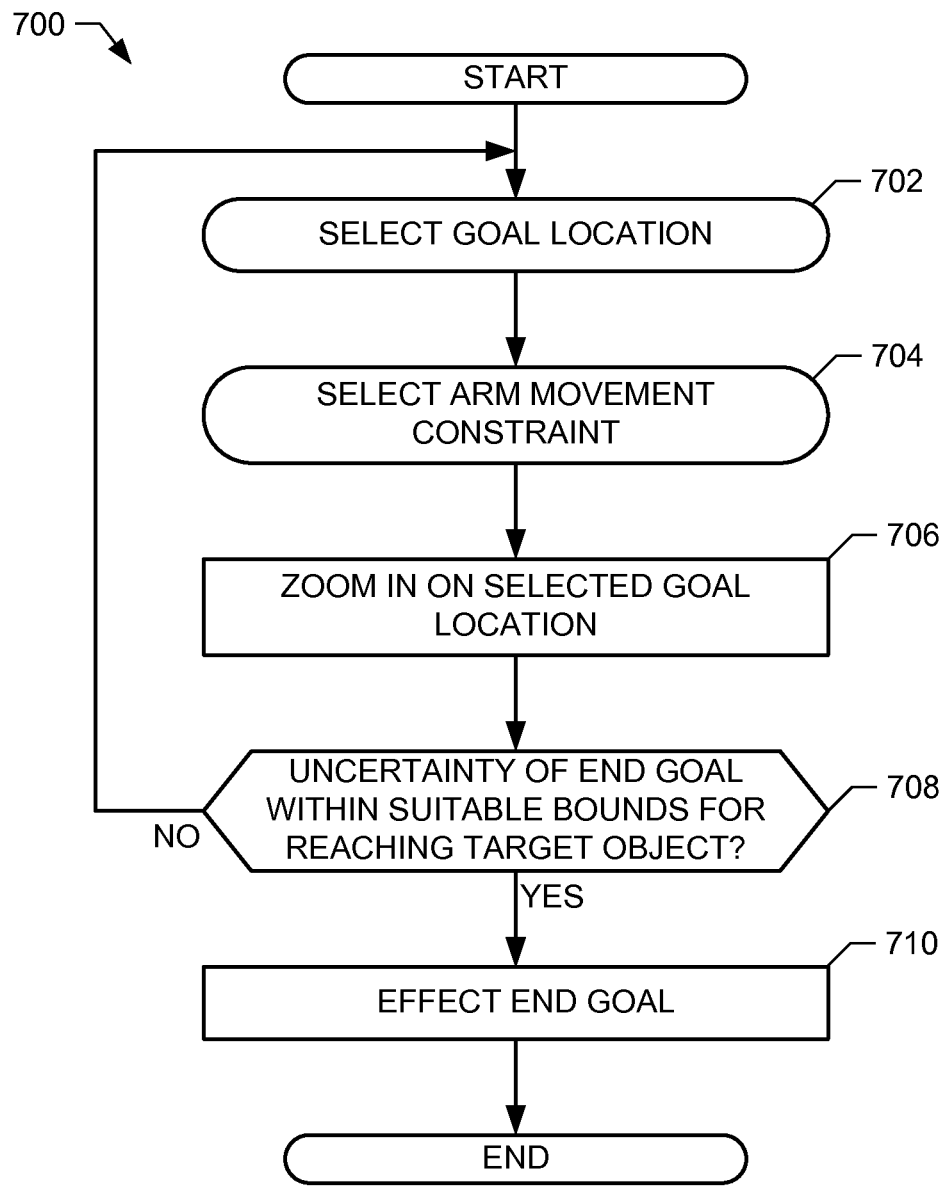
FIG. 7 is a flowchart representative of an example process that may be implemented to control a robot.
Figure 8:
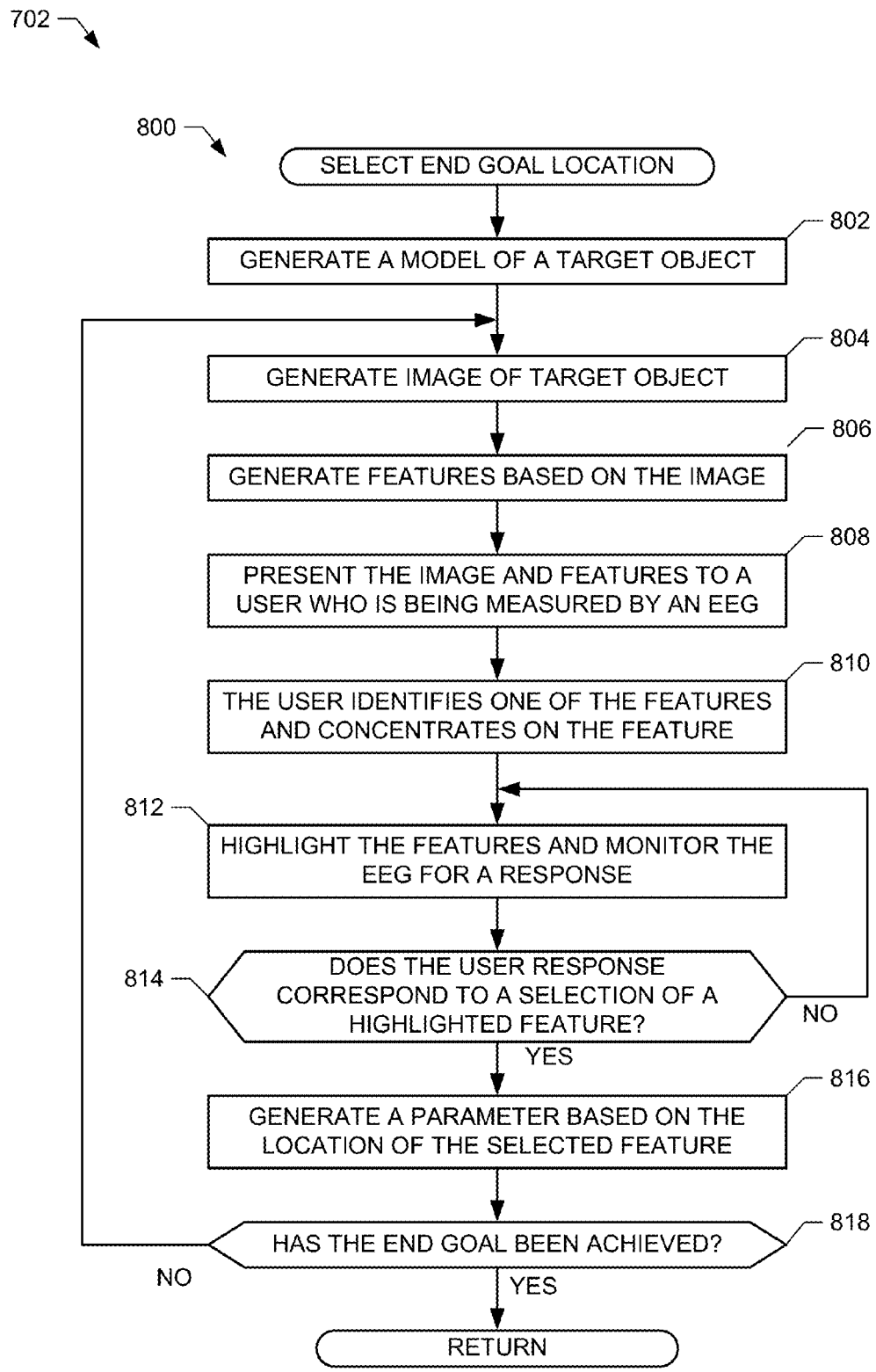
FIG. 8 is a flowchart representative of an example process that may be implemented to select an end goal for a robot.
Figure 9:
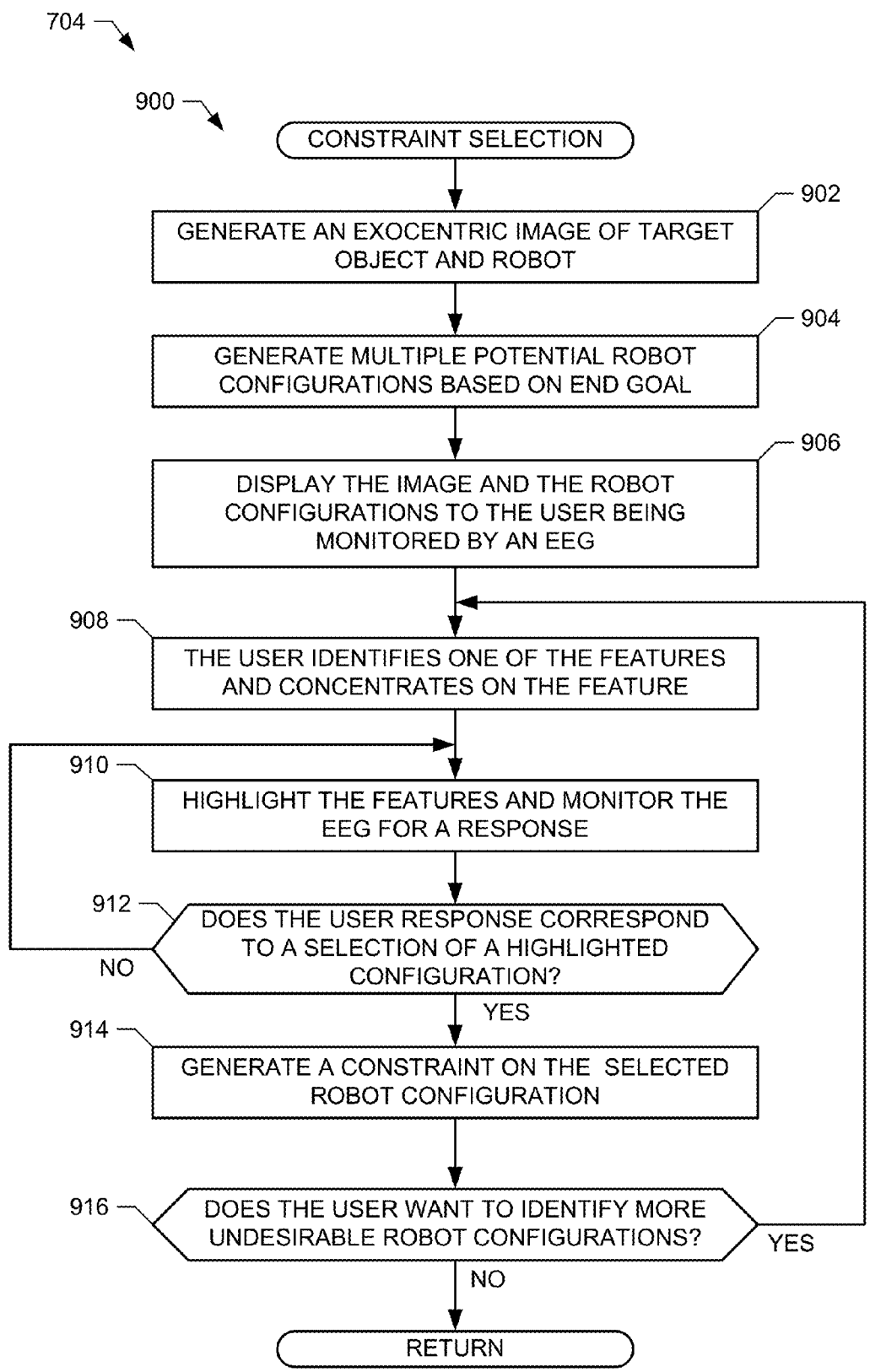
FIG. 9 is a flowchart representative of an example process that may be implemented to select constraints for a robot.

While an example manner of implementing the robot control system 100 and the goal/constraint selector 110 of FIGS. 1 and 2 is illustrated in FIGS. 7, 8, and 9 below, one or more of the elements, processes and/or devices illustrated in FIGS. 1 and 2 may be combined, divided, re-arranged, omitted, eliminated and/or implemented in any other way. Further, the example display 106, the example EEG system 108, the example goal/constraint selector 110, the example robot interface 112, the example robot controller 114, the example resolved-rate controller 116, the example object modeler 118, the example image generator 202, the example feature generator 204, the example feature and image presenter 206, the example parameter generator 208, the example classifier 210, and/or, more generally, the example robot control system 100 of FIGS. 1 and 2 may be implemented by hardware, software, firmware and/or any combination of hardware, software and/or firmware. Thus, for example, any of the display 106, the EEG system 108, the goal/constraint selector 110, the robot interface 112, the robot controller 114, the resolved-rate controller 116, the object modeler 118, the image generator 202, the feature generator 204, the feature and image presenter 206, the parameter generator 208, the classifier 210, and/or, more generally, the robot control system 100 of FIGS. 1 and 2 could be implemented by one or more circuit(s), programmable processor(s), application specific integrated circuit(s) (ASIC(s)), programmable logic device(s) (PLD(s)) and/or field programmable logic device(s) (FPLD(s)), etc.

When any of the appended claims are read to cover a purely software and/or firmware implementation, at least one of the example display 106, the example EEG system 108, the example goal/constraint selector 110, the example robot interface 112, the example robot controller 114, the example resolved-rate controller 116, the example object modeler 118, the example image generator 202, the example feature generator 204, the example feature and image presenter 206, the example parameter generator 208, the example classifier 210, and/or the example robot control system 100 are hereby expressly defined to include a tangible medium such as a memory, DVD, CD, etc. storing the software and/or firmware. Further still, the example robot control system 100 and/or the goal/constraint generator 110 of FIGS. 1 and 2 may include one or more elements, processes and/or devices in addition to, or instead of, those illustrated in FIGS. 1 and 2, and/or may include more than one of any or all of the illustrated elements, processes and devices.

FIG. 7 is a flowchart representative of an example process 700 that may be implemented to control a robot. The example process 700 begins by selecting an end goal location (block 702). The end goal location is used as an approximate position at which the robot (e.g., the robot 102 of FIG. 1) operates on the target object (e.g., the target object (e.g., the target object 103). The end goal location is a location at which the robot 102 is generally or particularly directed. When the user has selected an end goal (block 702), the process 700 then selects arm movement constraints for the robot (block 704). The arm movement constraints limit the physical configurations of the robot 102. The EEG system 108 of FIGS. 1 and 2 measures the brain activity of a user 104, which is then used by the classifier 210 of FIG. 2 to determine the selected robot arm configurations. Based on the classification, the goal/constraint selector 208 of FIG. 2 generates a robot arm constraint corresponding to the selected configurations.

After selecting the end goal (block 702) and the arm constraints (block 704), the process 700 zooms in on the selected goal location (block 706). As described above, the zooming in may occur by displaying a zoomed version of a previous image to the user and/or by generating a new image that is a zoomed version of the previous image. After zooming (block 706), the process 700 determines whether the uncertainty for the end goal location is within suitable bounds for reaching the target object 103 (block 708). If the end goal uncertainty is too large (block 708), the process 700 may return to block 706 to select another, more precise end goal.

If the process 700 determines that the uncertainty of the end goal location is within suitable bounds (block 708), the example process 700 effects the end goal (e.g., manipulates the target object 103) via the robot (block 710). When the robot arm has effected the end goal (block 710), the example process 700 may end. In some examples, block 704 may be performed after the robot 102 is zoomed within a close range of the target object 103 in block 708. In other words, the example process 700 iterates blocks 702, 706, and 708 to select a precise goal and then selects constraints on movement of the robot 102 with respect to the selected goal.

FIG. 8 is a flowchart representative of an example process 800 that may be implemented to select an end goal for a robot. The process 800 may be used to implement block 702 of the example process 700 illustrated in FIG. 7. The example process 800 (e.g., via the object modeler 118) generates a model of the target object 103 (block 802). The image generator 202 then generates an initial image of the target object 103 (e.g., the image 302 of FIG. 3, the image 402 of FIG. 4) (block 804).

The example feature generator 204 generates features (e.g., the features 303 and 304 of FIG. 3, the features 403 and 404 of FIG. 4) based on the image 302 (block 806). The feature and image presenter 206 then presents the image 302 (e.g., via the display 106) and the features 303 and 304 to a user 104 who is being measured by an EEG (e.g., the EEG system 108 of FIG. 1) (block 808). The user 104 identifies a particular feature 304 and concentrates on the feature 304 (block 810). The feature and image presenter 206 highlights each of the features 302-304 while the classifier 210 monitors the EEG measurements from the EEG system 108 of the user's 104 brain for a response (block 812). If the user's 104 response (e.g., a P300 signal response) does not correspond to a selection of a highlighted feature (e.g., the feature 304) (block 814), the process 800 returns to block 812 to highlight the features 302-304. However, if the response of the user 104 corresponds to a selection of a highlighted feature 304, the parameter generator 208 generates a parameter based on the location of the selected feature 304 (block 816).

The example process 800 then determines whether the end goal has been achieved (block 818). For example, if the parameter generator 208 has generated a parameter sufficiently focused on or within a desired precision of the end goal, the end goal has been achieved. When the end goal is achieved (block 818), the example process 800 ends and control returns to block 704 of FIG. 7. However, if the end goal has not been achieved (e.g., the parameters are not sufficiently focused on the end goal) (block 818), control returns to block 804 to generate another image (e.g., 306) of the target object 103 consistent with the new parameter.

FIG. 9 is a flowchart representative of an example process 900 that may be implemented to select constraints for a robot. The process 900 may be used to implement block 704 of the example process 700 illustrated in FIG. 7, which enters from block 702. To select one or more robot constraints, the example image generator 202 begins by generating (e.g., via the image generator 202) an exocentric image (e.g., the exocentric image 500 of FIG. 5) of the target object 103 and the robot (block 902). The example feature generator 204 then generates multiple robot configurations (e.g., the configurations 502, 504, and 506) to achieve the end goal selected in block 706 of FIG. 7 (block 904).

The feature and image presenter 206 then presents the image 500 (e.g., via the display 106) and the configurations 502-506 to the user 104 who is being measured by the EEG system 108 (block 906). The user 104 identifies a particular configuration 502 and concentrates on the configuration 502 (block 908). The feature and image presenter 206 highlights each of the configurations (e.g., 502-506) while the classifier 210 monitors the brain measurements from the EEG system 108 for a response. If the user's 104 response (e.g., a P300 signal response) does not correspond to a selection of a highlighted configuration (e.g., the configuration 502) (block 912), the process 900 returns to block 910 to highlight the configurations (e.g., 502-506). However, if the response by the user 104 corresponds to a selection of the highlighted configuration 502, the parameter generator 208 generates a constraint based on the position of the highlighted configuration 502 (block 914).

After the parameter generator 208 generates a constraint (block 914), the process 900 determines whether the user 104 wants to identify additional undesirable robot configurations (block 916). If the user 104 wants to identify additional configurations (block 916), control returns to block 908. If the user 104 has identified all undesirable configurations (block 916), the example process 900 may end, and control returns to block 706 of FIG. 7.

The example processes 700, 800, and 900 described above use an EEG system to measure the brain signals of a user and a classifier to detect a P300 brain signal from the measurements while emphasizing one feature in an image at a time. However, the example processes may be modified to use an EEG to detect a steady-state visual evoked potential (SSVEP) to allow the user to select a feature, robot configuration, or tracking point. Using an SSVEP, the goal/constraint selector 110 of FIG. 1 (via the display 106) displays multiple features or markers and flickers each feature or marker at a different rate between 5 Hz and 45 Hz. When the user gazes on a desired feature or marker, the classifier detects a particular SSVEP corresponding to the particular feature or marker from the EEG measurements of the user's brain. The parameter generator 208 then selects the feature or marker corresponding to the frequency evoking the SSVEP.

While the P300 evoked response provides a strong and readily detected signal, training may be required to calibrate or train the classifier 210 to a user's brain activity. During an example training procedure, approximately 250 images are shown to the user in a span of 30 seconds while the user selects predetermined images and the classifier 210 monitors the EEG system 108 to learn about the mental responses of the user 104. The user 104 may instruct the classifier 210 (e.g., via a button) when the classifier 210 is incorrect. Other types of measurements may require different training techniques. Some examples of training techniques that may be used are described in "Cortically-coupled computer vision for rapid image search," by Gerson, et al., published in *IEEE Transactions on Neural Systems and Rehabilitation Engineering*, [see also *IEEE Trans. on Rehabilitation Engineering*], Vol. 14, No. 2. (2006), pp. 174-179.

Figure 10:
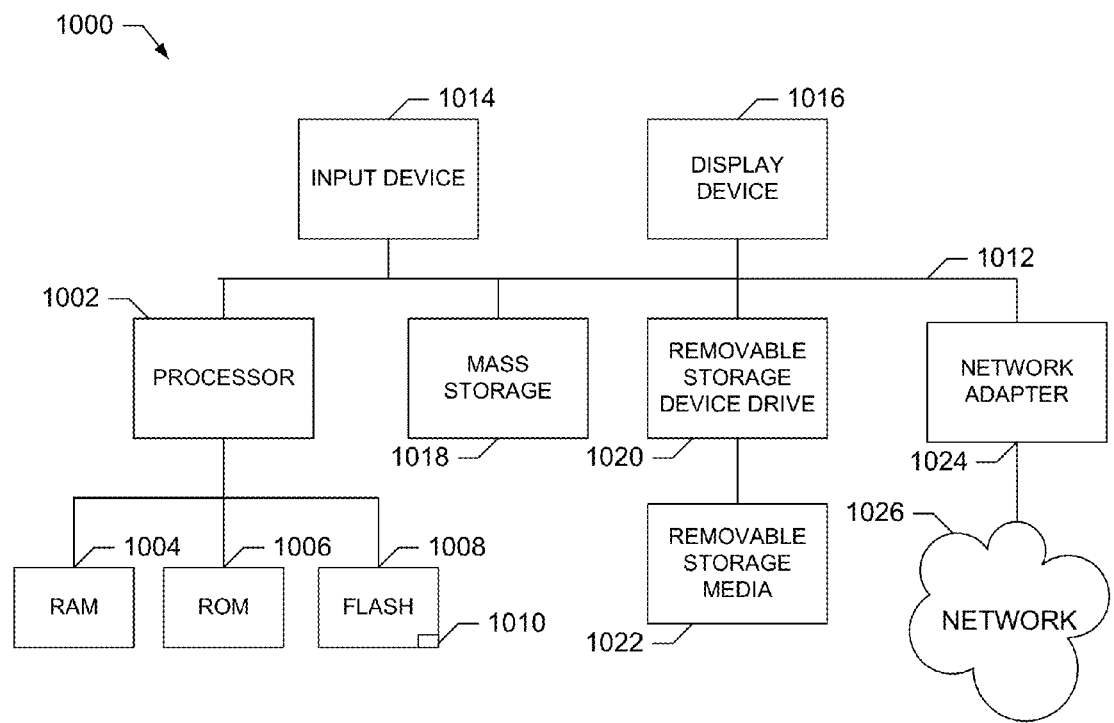
FIG. 10 is a diagram of an example processor system that may be used to implement the example systems and methods described herein.

FIG. 10 is a diagram of an example processor system 1000 that may be used to implement the example processes 700, 702, and/or 704 described herein, as well as the example display 106, the example EEG system 108, the example goal/constraint selector 110, the example robot interface 112, the example robot controller 114, the example resolved-rate controller 116, the example object modeler 118, the example image generator 202, the example feature generator 204, the example feature and image presenter 206, the example parameter generator 208, the example classifier 210, and/or, more generally, the example robot control system 100 of FIGS. 1 and 2.

Turning now to FIG. 10, an example processor system 1000 includes a processor 1002 having associated memories, such as a random access memory (RAM) 1004, a read only memory (ROM) 1006 and a flash memory 1008. The flash memory 1008 of the illustrated example includes a boot block 1010. The processor 1002 is coupled to an interface, such as a bus 1012 to which other components may be interfaced. In the illustrated example, the components interfaced to the bus 1012 include an input device 1014, a display device 1016, a mass storage device 1018 and a removable storage device drive 1020. The removable storage device drive 1020 may include associated removable storage media 1022 such as magnetic or optical media.

The example processor system 1000 may be, for example, a conventional desktop personal computer, a notebook computer, a workstation or any other computing device. The processor 1002 may be any type of processing unit, such as a microprocessor from the Intel® Pentium® family of microprocessors, the Intel® Itanium® family of microprocessors, and/or the Intel XScale® family of processors. The memories 1004, 1006 and 1008 that are coupled to the processor 1002 may be any suitable memory devices and may be sized to fit the storage demands of the system 1000. In particular, the flash memory 1008 may be a non-volatile memory that is accessed and erased on a block-by-block basis.

The input device 1014 may be implemented using a brain monitoring system such as an EEG system (e.g., the EEG system 108 of FIGS. 1 and 2), including an amplifier, a cap or other wearable device including a plurality of electrodes that may be worn by a user of the processing system 1000, and a data collection device, and/or any one or more of a keyboard, a mouse, a touch screen, a track pad, a barcode scanner or any other device that enables a user to provide information to the processor 1002.

The display device 1016 may be, for example, a liquid crystal display (LCD) monitor, a cathode ray tube (CRT) monitor or any other suitable device that acts as an interface between the processor 1002 and a user. The display device 1016 as pictured in FIG. 10 includes any additional hardware required to interface a display screen to the processor 1002.

The mass storage device 1018 may be, for example, a conventional hard drive or any other magnetic or optical media that is readable by the processor 1002.

The removable storage device drive 1020 may, for example, be an optical drive, such as a compact disk-recordable (CD-R) drive, a compact disk-rewritable (CD-RW) drive, a digital versatile disk (DVD) drive or any other optical drive. It may alternatively be, for example, a magnetic media drive. The removable storage media 1022 is complimentary to the removable storage device drive 1020, inasmuch as the media 1022 is selected to operate with the drive 1020. For example, if the removable storage device drive 1020 is an optical drive, the removable storage media 1022 may be a CD-R disk, a CD-RW disk, a DVD disk or any other suitable optical disk. On the other hand, if the removable storage device drive 1020 is a magnetic media device, the removable storage media 1022 may be, for example, a diskette or any other suitable magnetic storage media.

Although this patent discloses example systems including software or firmware executed on hardware, it should be noted that such systems are merely illustrative and should not be considered as limiting. For example, it is contemplated that any or all of these hardware and software components could be embodied exclusively in hardware, exclusively in software, exclusively in firmware or in any combination of hardware, firmware and/or software. Accordingly, while the above specification described example systems, methods, apparatus, and articles of manufacture, the examples are not the only way to implement such systems, methods, apparatus, and articles of manufacture. While the foregoing describes example processes, the processes may be also implemented as computer-readable instructions encoded onto a machine-accessible medium. Therefore, although certain example systems, methods, apparatus, and articles of manufacture have been described herein, the scope of coverage of this patent is not limited thereto. On the contrary, this patent covers all systems, methods, apparatus and articles of manufacture fairly falling within the scope of the appended claims either literally or under the doctrine of equivalents.

What is claimed is:

1. A method to control a robot, comprising:
presenting an object to a user, the object corresponding to a goal to be effected by a robot;
emphasizing a portion of the object;
identifying a first brain signal corresponding to a first mental response of the user to the emphasized portion;
determining whether the first mental response corresponds to a selection of the emphasized portion by the user; and
controlling the robot via a processor based on determining that the first mental response corresponds to a selection of the emphasized portion.

2. A method as defined in claim 1, further comprising:
presenting a plurality of physical configurations capable of reaching the goal to the user;
emphasizing one of the plurality of physical configurations of the object;
identifying a second brain signal corresponding to a second mental response of the user to an emphasized physical configuration;
determining whether the second mental response corresponds to a selection of the emphasized physical configuration by the user; and
generating a constraint on the robot corresponding to the emphasized physical configuration in response to determining the emphasized physical configuration.

3. A method as defined in claim 1, wherein presenting the object to the user comprises generating an image of the object, selecting a plurality of features of the object, and displaying the object and the features to the user.

4. A method as defined in claim 1, wherein identifying the first brain signal comprises monitoring an electroencephalogram (EEG) for at least one of a P300 brain signal or a steady-state visual evoked potential.

5. A method as defined in claim 4, wherein controlling the robot is in response to receiving the P300 brain signal in response to the emphasized portion.

6. A method as defined in claim 1, further comprising:
presenting a second view of the object to the user, wherein the second view is based on the emphasized portion;
emphasizing a second portion of the second view;
identifying a second brain signal corresponding to a second mental response of the user to the emphasized second portion; and
determining whether the second mental response corresponds to a selection of the emphasized second portion by the user, wherein controlling the robot is based on the emphasized second portion.

7. A method as defined in claim 1, wherein presenting the object to the user comprises displaying a plurality of markers at different locations, the markers comprising different frequencies.

8. A robot control apparatus, comprising:
a selector to:
  generate a first image of an object;
  identify a plurality of features of the object based on the first image;
  emphasize one of the plurality of features to a user;
  modify the first image based on a feature selected by the user;
  present a plurality of physical configurations to the user; and
  emphasize one of the plurality of physical configurations to the user;
a user response interface, in communication with the selector, to identify a user brain signal in response to an emphasized feature or physical configuration; and
a robot interface to generate control information to control a robot based on at least one of the emphasized feature or the emphasized physical configuration corresponding to an identified brain signal.

9. A robot control apparatus as defined in claim 8, wherein the user response interface is to identify a user brain signal corresponding to a negative selection of the emphasized physical configuration.

10. A robot control apparatus as defined in claim 8, wherein the selector comprises:
an image generator to generate a current reference image based on the object and one or more parameters;
a feature generator to generate features of the object based on the current reference image;
a feature/image presenter to provide the reference image and the features to a user display; and
a parameter generator coupled to generate the one or more parameters of the reference image based on the object.

11. A robot control apparatus as defined in claim 8, wherein the user response interface comprises an electroencephalogram (EEG).

12. A robot control apparatus as defined in claim 8, wherein the selector is to modify the first image by generating a second image based on the feature selected by the user and identifies a second plurality of features based on the second image, the user response interface to identify a second user brain signal in response to a second emphasized feature.

13. A robot control apparatus as defined in claim 12, wherein the second image is a zoomed in version of the first image.

14. A tangible machine readable storage medium comprising machine readable instructions which, when executed, cause a machine to:

present an object to a user, the object corresponding to a goal to be effected by a robot;
emphasize a portion of the object;
identify a first brain signal corresponding to a first mental response of the user to the emphasized portion;
determine whether the first mental response corresponds to a selection of the emphasized portion by the user; and
control the robot based on determining that the first mental response corresponds to a selection of the emphasized portion.

15. A storage medium as defined in claim 14, wherein the instructions, when executed, further cause the machine to:
present a plurality of physical configurations capable of reaching the goal to the user;
emphasize one of the plurality of physical configurations of the object;
identify a second brain signal corresponding to a second mental response of the user to an emphasized physical configuration;
determine whether the second mental response corresponds to a selection of the emphasized physical configuration by the user; and
generate a constraint on the robot corresponding to the emphasized physical configuration in response to determining the emphasized physical configuration.

16. A storage medium as defined in claim 14, wherein presenting the object to the user comprises generating an image of the object, selecting a plurality of features of the object, and displaying the object and the features to the user.

17. A storage medium as defined in claim 16, wherein emphasizing the features of the object comprises selecting one of the plurality of features and performing at least one of flashing the selected feature over the image or flickering the selected feature over the image.

18. A storage medium as defined in claim 14, wherein identifying the first brain signal comprises monitoring an electroencephalogram (EEG) for at least one of a P300 brain signal or a steady-state visual evoked potential.

19. An article of manufacture as defined in claim 14, wherein identifying the first mental response of the user comprises monitoring an electroencephalogram (EEG) for the first brain signal corresponding to one of a plurality of markers, the plurality of markers being displayed at different respective locations and being flickered at different respective frequencies.

20. A storage medium as defined in claim 19, wherein controlling the robot comprises controlling the robot to move toward the portion of the object corresponding to the one of the markers, the one of the markers corresponding to the first brain signal.

* * * * *